(12) United States Patent
Tanaka

(10) Patent No.: US 8,044,216 B2
(45) Date of Patent: Oct. 25, 2011

(54) FLUOROBORON COMPOUND, AMINOMETHYLATING AGENT FOR AROMATIC RING MADE OF THE SAME, AND PRODUCTION METHOD OF COMPOUND CONTAINING AMINOMETHYL AROMATIC RING USING AMINOMETHYLATING AGENT

(75) Inventor: Keigo Tanaka, Tsukuba (JP)

(73) Assignee: Eisai R&D Management Co., Ltd., Tokyo (JP)

(*) Notice: Subject to any disclaimer, the term of this patent is extended or adjusted under 35 U.S.C. 154(b) by 1053 days.

(21) Appl. No.: 11/822,832

(22) Filed: Jul. 10, 2007

(65) Prior Publication Data
US 2008/0015351 A1 Jan. 17, 2008

Related U.S. Application Data

(60) Provisional application No. 60/819,628, filed on Jul. 11, 2006.

(30) Foreign Application Priority Data

Jul. 11, 2006 (JP) .................................. 2006-190813

(51) Int. Cl.
*C07D 209/48* (2006.01)
(52) U.S. Cl. ....................................................... 548/476
(58) Field of Classification Search .................... 548/476
See application file for complete search history.

(56) References Cited

U.S. PATENT DOCUMENTS
2007/0105943 A1 5/2007 Nakamoto et al.

FOREIGN PATENT DOCUMENTS
WO WO-2005/033079 A1 4/2005

OTHER PUBLICATIONS

Byrn et al. Solid-State Chemistry of Drugs, 2d (1999), Chapters 10 & 11.*
A.M. Rouhi, Chem. & Eng. News, Feb. 24, 2003, 81(8), 32-35.*
Ali et al. (Tetrahedron, 60 (2004), 4773-4780).*
Molander et al. (Org. Lett., 9 (2007), 1597-1600).*
Molander et al. (Aldrichimica Acta, 38 (2005), 49-56).*
Jensen et al., Organic Letters, vol. 2, No. 8, 2000, pp. 1081-1084.
Molander et al., Organic Letters, vol. 8, No. 10, 2006, pp. 2031-2034.
Matteson et al., The Journal of Organic Chemistry, vol. 33, No. 8, Aug. 1968, pp. 3055-3060.
Batey et al., Tetrahedron Letters, vol. 42, 2001, pp. 9099-9103.
Bose et al., Synthesis, No. 1, 1999, pp. 66-68.
Davis et al., Tetrahedron Letters, vol. 33, No. 52, 1992, pp. 8125-8126.
Ali et al., Tetrahedron, vol. 60, 2004, pp. 4773-4780.
Molander et al., Organic Letters, vol. 9, No. 8, 2007, pp. 1597-1600.
Molander et al., Organic Letters, vol. 8, No. 13, 2006, pp. 2767-2770.
Danishefsky et al., "The B-Alkyl Suzuki-Miyaura Cross-Coupling Reaction: Development, Mechanistic Study, and Applications in Natural Product Synthesis", Angew. Chem. Int. Ed., vol. 40, pp. 4544-4568, 2001.
Jamieson et al., "The first enantioselective synthesis of the amino acid, (2S,3S,4R)-γ-hydroxyisoleucine using a palladium(II) catalysed 3,3-sigmatropic rearrangement", Org. Biomol. Chem., vol. 2, pp. 808-809, Feb. 19, 2004.
Kirsch et al., "Catalytic Asymmetric Synthesis of Chiral Allylic Esters", J. Am. Chem. Soc., vol. 127, pp. 2866-2867, 2005 (Published on web Feb. 12, 2005).
Kirsch et al., "Monomeric Cobalt Oxazoline Palladacycles (COP). Useful Catalysts for Catalytic Asymmetric Rearrangement of Allylic Trichloroacetimidates", J. Org. Chem., vol. 69, No. 23, pp. 8101-8104, 2004 (Published on web Oct. 12, 2004).
Norrby et al., "Deconvoluting the Memory Effect in Pd-Catalyzed Allylic Alkylation: Effect of Leaving Group and Added Chloride", Chem. Eur. J., vol. 12, pp. 5352-5360, 2006 (Published online Apr. 25, 2006).

* cited by examiner

*Primary Examiner* — Robert Havlin
(74) *Attorney, Agent, or Firm* — Birch, Stewart, Kolasch & Birch, LLP

(57) ABSTRACT

A production method of a compound containing a primary, secondary, or tertiary aminomethyl aromatic ring of the present invention includes: using a fluoroboron compound or a dimer thereof, or solvates thereof, which are represented by a formula (I):

$$Ra(Rb)N-CH_2-BF_3M \qquad (I)$$

as an aminomethylating agent for an aromatic ring; and reacting the aminomethylating agent with an aromatic ring-containing compound, which can react with the aminomethylating agent, under the presence of a metal catalyst such as a palladium compound so as to perform the direct aminomethylation of the aromatic ring.

4 Claims, No Drawings

FLUOROBORON COMPOUND, AMINOMETHYLATING AGENT FOR AROMATIC RING MADE OF THE SAME, AND PRODUCTION METHOD OF COMPOUND CONTAINING AMINOMETHYL AROMATIC RING USING AMINOMETHYLATING AGENT

CROSS-REFERENCE TO RELATED APPLICATION

This application is non-provisional application claiming the benefit pursuant to 35 U.S.C. 119(e)(1) of U.S. Provisional Application No. 60/819628, filed Jul. 11, 2006, and claims priority to Japanese Patent Application No. 2006-190813, filed Jul. 11, 2006, the contents of which are incorporated herein by reference.

BACKGROUND OF THE INVENTION

1. Field of the Invention

The present invention relates to a fluoroboron compound which is useful as an aminomethylating agent to directly introduce a primary, secondary, or tertiary aminomethyl group to an aromatic ring, and to an aminomethylating reaction for an aromatic ring using the fluoroboron compound.

2. Description of Related Art

The structure of an aromatic ring containing an aminomethyl group (hereinafter, may be referred to as an "aminomethyl aromatic ring") is widely used in medical compounds, and has high industrial applicability. For example, the patent document 1, which relates to a novel antifungal agent, discloses a compound containing an aminomethyl aromatic ring in a part of the chemical structure (hereinafter, may be referred to as an "aminomethyl aromatic compound"). Of compounds containing an aminomethyl aromatic ring, a compound containing a primary aminomethyl aromatic ring is frequently used as a precursor for a compound containing a secondary or tertiary aminomethyl aromatic ring, and therefore, many types of the compounds is sold as a reagent in a market.

Conventionally, as a method of obtaining a compound containing the aforementioned chemical structure, a synthetic method, which uses a reduction reaction, and a synthetic method, which uses a compound containing a halomethyl group-containing aromatic ring as a precursor, have been reported.

A reaction, which uses a metal catalyst to directly introduce an aminomethyl group to an aromatic halide substrate such as chlorobenzene, has never been reported as a production method of an aminomethyl aromatic ring.

As an aminomethylating reaction using a metal catalyst, a sulfonylaminomethylating reaction for enol triflate using an organotin compound was reported as disclosed in non-patent document 1.

Also, the non-patent document 2 discloses an aminomethylfluoroboron compound, and the non-patent document 3 discloses an aminomethylboron compound whose structure is similar to that of an aminomethylfluoroboron compound. However, an aminomethylation reaction for an aromatic ring using these compounds has never been reported.

[Patent Document 1] PCT International Publication No. WO2005/033079
[Non-Patent Document 1] Org. Lett., 2000, 2, 1081
[Non-Patent Document 2] Org. Lett., 2006, 8, 2031
[Non-Patent Document 3] J. Org. Chem., 1968, 33, 3055

SUMMARY OF THE INVENTION

In the synthesis of an aminomethyl aromatic ring, which uses the aforementioned reduction reaction, there is a problem in that it is difficult to obtain an aimed compound in high yield when using a substrate which is not suitable for a reduction reaction. Also, in an aminomethylation method of an aromatic ring, which uses a halomethyl group-containing aromatic ring as a precursor, there is a problem in that attention should be paid to handling because the chemical stability of the precursor itself is poor. Therefore, the industrial use of this aminomethylation method is limited. Moreover, apart from or in addition to the aforementioned problems, it has been desired to use an aromatic halide such as chlorobenzene, which is inexpensive and has a lot of types of commercially available reagents, as a precursor in the case where an aminomethyl aromatic ring is synthesized.

An organotin compound as disclosed in non-patent document 1 lacks versatility because the chemical structure is limited to cyclic sulfonamide. In this case, it is feared that the toxic problem of the organotin compound may occur, and so it is not suitable for industrial use.

Non-patent document 2 discloses several aminomethylfluoroboron compounds, but does not teach or suggest that these compounds are used in an aminomethylation reaction for an aromatic ring at all. In addition, these compounds do not include a protected primary aminomethylfluoroboron compound.

In the same way, non-patent document 3 discloses primary aminomethylboronic acid which is protected with imide, but does not teach or suggest that this compound is used in an aminomethylation reaction for an aromatic ring at all.

An object of the present invention is to solve the aforementioned problems.

In other words, objects of the present invention are to provide a compound which can be used as a highly versatile reactant enabling direct introduction of a primary, secondary, or tertiary aminomethyl group to an aromatic ring; an aminomethylating agent for an aromatic compound, which is made of the compound; and a production method of a compound containing aminomethyl aromatic ring using the aminomethylating agent.

The present inventors found that an aminomethylation reaction for an aromatic ring can be performed by reacting a fluoroboron compound or a dimer thereof, or solvates thereof with an aromatic ring-containing compound under the presence of a metal catalyst, and completed the present invention.

A detailed aspect of a fluoroboron compound of the present invention is a fluoroboron compound or a dimer of the fluoroboron compound, or solvates of the fluoroboron compound and the dimer, the compound being represented by a formula (I):

$$Ra(Rb)N\text{---}CH_2\text{---}BF_3M \qquad (I)$$

(wherein Ra and Rb each independently represents a group selected from the group consisting of a hydrogen atom, a substituted or unsubstituted $C_{1-6}$ alkyl group, a substituted or unsubstituted cycloalkyl group, a substituted or unsubstituted heterocyclic group, a substituted or unsubstituted heteroaryl group, a substituted or unsubstituted aryl group, a substituted or unsubstituted aralkyl group, and a protecting group of an amino group; a protecting group of an amino group formed by joining a nitrogen atom bonded with Ra and Rb; or a substituted or unsubstituted heterocyclic group, which may contain 1 or more heteroatom by an optional choice, formed by joining a nitrogen atom bonded with Ra and Rb, and M represents an alkali metal cation, $[N(R^1)(R^2)(R^3)(R^4)]^+$, or $[P(R^1)(R^2)(R^3)(R^4)]^+$ ($R^1$, $R^2$, $R^3$ and $R^4$ each independently represents a $C_{1-6}$ alkyl group or a $C_{7-15}$ aralkyl group) (wherein potassium n-butylaminomethyl trifluoroborate, potassium cyclohexylaminomethyl trifluoroborate, potassium N-pyrrolidinylmethyl trifluoroborate, and potassium N-piperidylmethyl trifluoroborate are removed)).

However, in an aminomethylating agent used in the aminomethylation reaction for an aromatic ring described below, the use of potassium n-butylaminomethyl trifluoroborate, potassium cyclohexylaminomethyl trifluoroborate, potassium N-pyrrolidinylmethyl trifluoroborate, and potassium N-piperidylmethyl trifluoroborate is included in the scope of the present invention.

In a compound represented by the formula (I), it is preferable that Ra and Rb each independently represent a group selected from the group consisting of the hydrogen atom, the $C_{1-6}$ alkyl group, and the protecting group of the amino group; the protecting group of the amino group formed by joining the nitrogen atom bonded with Ra and Rb; or the substituted or unsubstituted heterocyclic group, which may contain 1 or more heteroatom by an optional choice, formed by joining the nitrogen atom bonded with Ra and Rb.

In a compound represented by the formula (I), it is preferable that Ra and Rb each independently represent the hydrogen atom or the protecting group of the amino group.

In addition, the protecting group of the amino group is preferably a cyclic imide-based protecting group, an amide-based protecting group, or a carbamate-based protecting group, and more preferably the carbamate-based protecting group.

In addition, the protecting group is preferably a phthaloyl group, a formyl group, or a t-butyloxycarbonyl group.

A preferable aspect of a dimer of a compound represented by the formula (I) is a compound or a solvate of the compound, which is represented by a formula (II):

(II)

(wherein Ra represents a hydrogen atom, a substituted or unsubstituted $C_{1-6}$ alkyl group, a substituted or unsubstituted cycloalkyl group, a substituted or unsubstituted heterocyclic group, a substituted or unsubstituted heteroaryl group, a substituted or unsubstituted aryl group, a substituted or unsubstituted aralkyl group, and a protecting group of an amino group, and M represents an alkali metal cation, $[N(R^1)(R^2)(R^3)(R^4)]^+$, or $[P(R^1)(R^2)(R^3)(R^4)]^+$ ($R^1$, $R^2$, $R^3$ and $R^4$ each independently represents a $C_{1-6}$ alkyl group or a $C_{7-15}$ aralkyl group)).

In the formula (II), Ra preferably represents the protecting group of the amino group.

In addition, the protecting group of the amino group is preferably an amide-based protecting group or a carbamate-based protecting group, and more preferably the carbamate-based protecting group.

In addition, the protecting group of the amino group is preferably a t-butyloxycarbonyl group.

As a compound represented by the formula (I), a compound or a solvate of the compound, which is represented by a formula (III):

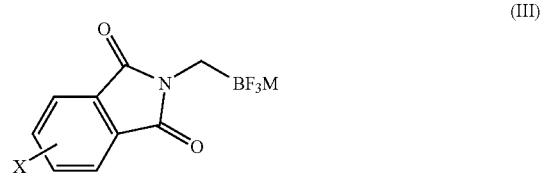

(III)

(wherein M represents an alkali metal cation, $[N(R^1)(R^2)(R^3)(R^4)]^+$, or $[P(R^1)(R^2)(R^3)(R^4)]^+$ ($R^1$, $R^2$, $R^3$ and $R^4$ each independently represents a $C_{1-6}$ alkyl group or a $C_{7-15}$ aralkyl group), and X represents a hydrogen atom, a $C_{1-6}$ alkyl group, or a nitro group).

In the formula (III), X preferably represents the hydrogen atom.

Moreover, in a compound or a dimer of the compound, or solvates of the compound and the dimer, which are represented by the formula (I), (II), or (III), M preferably represents the alkali metal cation.

The aforementioned M preferably represents a potassium ion or a sodium ion.

The present invention further relates to a primary, secondary, or tertiary aminomethylating agent selected from the group consisting of a fluoroboron compound and a dimer of the fluoroboron compound, and solvates of the fluoroboron compound and the dimer.

As aminomethylation, primary aminomethylation is particularly exemplified.

As an aminomethylating agent of the present invention, a compound represented by the formula (I) is exemplified.

In a compound represented by the formula (I), which is used as an aminomethylating agent, Ra and/or Rb are preferably the hydrogen atom or the protecting group of the amino group.

In the aminomethylating agent, the protecting group of the amino group is preferably a cyclic imide-based protecting group, an amide-based protecting group, or a carbamate-based protecting group, and more preferably the carbamate-based protecting group.

In the aminomethylating agent, the protecting group of the amino group is preferably a phthaloyl group, a formyl group, or a t-butyloxycarbonyl group.

As an aminomethylating agent of the present invention, a compound represented by the formula (II) is further exemplified.

In an aminomethylating agent represented by the formula (II), Ra preferably represents the protecting group of the amino group.

Moreover, in an aminomethylating agent represented by the formula (II), the protecting group of the amino group is preferably an amide-based protecting group or a carbamate-based protecting group, and more preferably the carbamate-based protecting group.

Moreover, in an aminomethylating agent represented by the formula (II), the protecting group of the amino group is preferably t-butyloxycarbonyl group.

As an aminomethylating agent of the present invention, a compound represented by the formula (III) is further exemplified.

In an aminomethylating agent represented by the formula (III), X preferably represents the hydrogen atom.

In an aminomethylating agent represented by the formula (III), M preferably represents the alkali metal cation.

In an aminomethylating agent represented by the formula (III), M preferably represents a potassium ion or a sodium ion.

In addition, the present invention provides a production method of a compound containing a primary, secondary, or tertiary aminomethyl aromatic ring, and this production method is characterized by reacting the aforementioned aminomethylating agent with an aromatic ring-containing compound, which can cause a coupling reaction with the aminomethylating agent, under the presence of a metal catalyst which is effective for the coupling reaction.

According to the present invention, the aforementioned objects can be solved.

In other words, according to the present invention, a primary, secondary, or tertiary aminomethyl group can be directly introduced to an aromatic ring. An aminomethylation method of an aromatic ring of the present invention does not use a reduction reaction, and therefore, it is possible to use a substrate which is unstable for a reduction reaction. Also, there is no need to use a compound containing a halomethyl group-containing aromatic ring which is poor in chemical stability.

In addition to the aforementioned advantageous effects, it is possible to use an aromatic halide such as chlorobenzene which is inexpensive and sold in a market abundantly.

Accordingly, a fluoroboron compound of the present invention is useful as a reactive reagent which can introduce an aminomethyl group, particularly a primary aminomethyl group, to an aromatic ring.

DETAILED DESCRIPTION OF THE INVENTION

Hereinafter, the present invention is described in detail.

The present invention is a fluoroboron compound or a solvate thereof, which can introduce an aminomethyl group to an aromatic ring.

Next, the terms used in the present specification will be explained.

In the present invention, the term of "an aromatic ring" means a cyclic group having aromatic property, may be a monocyclic ring or a condensed ring, may be an aromatic hydrocarbon cyclic group (aryl group) or an aromatic heterocyclic group (heteroaryl group), and may further contain a substituent group. Examples of an aromatic ring include a benzene ring, a naphthalene ring, a furan ring, a thiophene ring, a pyrrole ring, an imidazole ring, a triazole ring, a tetrazole ring, a thiazole ring, a pyrazole ring, an oxazole ring, an isoxazole ring, an isothiazole ring, a furazan ring, a thiadiazole ring, an oxadiazole ring, a pyridine ring, a pyrazine ring, a pyridazine ring, a pyrimidine ring, a triazin ring, a purine ring, a pteridine ring, a quinoline ring, an isoquinoline ring, a naphthyridine ring, a quinoxaline ring, a cinnoline ring, a quinazoline ring, a phthalazine ring, an imidazopyridine ring, an imidazothiazole ring, an imidazooxazole ring, a benzothiazole ring, a benzoxazole ring, a benzimidazole ring, an indole ring, a be isoindole ring, an indazole ring, a pyrrolepyridine ring, a thienopyridine ring, a furopyridine ring, a benzothiadiazole ring, a benzoxadiazole ring, a pyridopyrimidine ring, a benzofuran ring, a benzothiophene ring, a benzo[1,3]dioxole ring, and a thienofuran ring. However, an aromatic ring is not limited to these.

In the present specification, the term of "an aminomethyl group" includes a primary aminomethyl group, a secondary aminomethyl group, and a tertiary aminomethyl group, and further includes a primary aminomethyl group and a secondary aminomethyl group in which an amino group is protected by a protecting group. Also, the term of "a primary, secondary, or tertiary aminomethyl group" means a methyl group substituted with a primary amino group, a secondary amino group, or a tertiary amino group, respectively, and a primary aminomethyl group or a secondary aminomethyl group may be protected by a protecting group described below.

In the present specification, the term of "a protecting group of an amino group" means a well-known protecting group of an amino group, and examples thereof include an amide-based protecting group such as a formyl group, an acetyl group, a benzoyl group, a nicotinoyl group, a picolinoyl group, a trichloroacetyl group, or a trifluoroacetyl group; a cyclic imide-based protecting group such as a phthaloyl group or 2,3-diphenyl maleoyl group; a sulfonamide-based protecting group such as a p-toluenesulfonyl group; and a carbamate-based protecting group such as a t-butyloxycarbonyl group, a methyloxycarbonyl group, an ethyloxycarbonyl group, an allyloxycarbonyl group, a benzyloxycarbonyl group, a p-methoxybenzylcarbonyl group, a p-nitrobenzyloxycarbonyl group, or a 9-fluorenylmethyloxycarbonyl group. However, a protecting group of an amino group is not limited to these. Preferable examples of a protecting group of an amino group include a formyl group, a t-butyloxycarbonyl group, and a phthaloyl group.

In the present specification, the term of "aminomethylation" means introduction of a group to an aromatic ring, the group being selected from the group consisting of a primary aminomethyl group, a secondary aminomethyl group, a tertiary aminomethyl group, a primary aminomethyl group in which an amino group is protected by a protecting group, and a secondary aminomethyl group in which an amino group is protected by a protecting group.

In the present specification, the term of "an aminomethyl aromatic ring" means an aromatic ring in which the aforementioned aminomethylation is performed.

In the present specification, the term of "an alkali metal" means a metal atom which belongs to Group 1 of the periodic table, and examples thereof include lithium, sodium, and potassium, and sodium and potassium are preferable.

In the present specification, the term of "a $C_{1-6}$ alkyl group" means a straight-chain or branched alkyl group having 1 to 6 carbon atoms which is a monovalent group derived by removing any one of hydrogen atom from an aliphatic hydrocarbon having 1 to 6 carbon atoms. Examples of a $C_{1-6}$ alkyl group include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group. Of these, a methyl group, an ethyl group, a 1-propyl group, a 2-propyl group, a 2-methyl-1-propyl group, a 2-methyl-2-propyl group, a 1-butyl group, and a 2-butyl group are preferable, and a methyl group and an ethyl group are more preferable.

In the present specification, the term of "a cycloalkyl group" means a saturated hydrocarbon group having cyclic chemical structure formed of 3 or more carbon atoms. The number of carbon atoms constituting a cycloalkyl group is not particularly limited as long as it is 3 or more. The number of carbon atoms is preferably 3 to 12, and more preferably 3 to 6. Specific examples of a cycloalkyl group include a cyclopropyl group, a cyclobutyl group, a cyclopentyl group, a cyclohexyl group, and a decahydronaphthalene group.

In the present specification, the term of "an aralkyl group" means an alkyl group bonded with an aryl group. The term of "a $C_{7-15}$ aralkyl group" means a functional group in which the aforementioned "$C_{1-6}$ alkyl group" is bonded with a $C_{6-14}$ aryl group (which means an aromatic hydrocarbon cyclic group having 6 to 14 carbon atoms, and examples thereof include a phenyl group, a 1-naphthyl group, a 2-naphthyl group, an indenyl group, an azulenyl group, a heptalenyl group, an indacenyl group, a biphenylenyl group, an acenaphtylenyl group, a fluorenyl group, a phenalenyl group, a phenanthrenyl group, and an anthracenyl group). Examples of a $C_{7-15}$ aralkyl group include a benzyl group, an α-naphthylmethyl group, a β-naphthylmethyl group, an indenylmethyl group, a 1-phenethyl group, a 2-phenethyl group, a 1-naphthylethyl group, a 2-naphthylethyl group, a 1-phenylpropyl group, a 2-phenylpropyl group, a 3-phenylpropyl group, a 1-naphthylpropyl group, a 2-naphthylpropyl group, a 3-naphthylpropyl group, a 1-phenylbutyl group, a 2-phenylbutyl group, a 3-phenylbutyl group, a 4-phenylbutyl group, a 1-naphthylbutyl group, a 2-naphthylbutyl group, a 3-naphthylbutyl group, a 4-naphthylbutyl group, a 1-phenylpentyl group, a 2-phenylpentyl group, a 3-phenylpentyl group, a 4-phenyl pentyl group, a 5-phenylpentyl group, a 1-naphthylpentyl group, a 2-naphthylpentyl group, a 3-naphthylpentyl group, a 4-naphthylpentyl group, a 5-naphthylpentyl group, a 1-phenylhexyl group, a 2-phenylhexyl group, a 3-phenylhexyl group, a 4-phenylhexyl group, a 5-phenylhexyl group, a 6-phenylhexyl group, a 1-naphthylhexyl group, a 2-naphthylhexyl group, a 3-naphthylhexyl group, a 4-naphthylhexyl group, a 5-naphthylhexyl group, and a 6-naphthyl hexyl group. Preferable examples of a $C_{7-15}$ aralkyl group include a benzyl group, 1-phenethyl group, and 2-phenethyl group.

In the present specification, the term of "a heterocyclic group" means a non-aromatic hydrocarbon cyclic group having 1 or more heteroatoms, and is distinguished from a heteroaryl group. A heteroatom is not particularly limited, and typical examples thereof include an oxygen atom, a nitrogen atom, and a sulfur atom. A heterocyclic group may have 2 types or more of heteroatoms in 1 ring. A heterocyclic ring is preferably formed of 3 to 10 atoms which include a heteroatom and a carbon atom constituting a ring, and more preferably formed of 5 to 7 atoms. A heterocyclic ring may be formed of a single ring, or 2 or more rings. Specific examples of a heterocyclic group include a tetrahydrofuranyl group, a tetrahydropyranyl group, a piperidinyl group, a pyrrolidinyl group and a morpholinyl group.

In the present specification, the term of "a heteroaryl group" means an heteroaromatic cyclic group having 1 or more heteroatoms. Examples of a heteroatom include an oxygen atom, a nitrogen atom, and a sulfur atom. A heteroaryl group is preferably formed of 5 to 14 atoms, and more preferably formed of 5 or 6 atoms. Specific examples of a heteroaryl group include a furyl group, a thienyl group, a pyrrolyl group, an imidazolyl group, a pyrrolidyl group, an isoxazolyl group, a pyrazinyl group, and a pyrimidinyl group.

In the present specification, the term of "an aryl group" means the same as the term of "an aromatic ring" group.

In the present specification, the term of "substituted or unsubstituted" means that a substituent group may be contained by an optional choice. Examples of a substituent group include a halogen atom such as a fluorine atom, a chlorine atom, a bromine atom, or the iodine atom; an amino group; a mono- or di-alkylamino group such as a dimethylamino group, a diethylamino group, or a dibutylamino group; a nitro group; a cyano group; an alkyl group such as the aforementioned $C_{1-6}$ alkyl group; a $C_{1-6}$ alkoxy group such as a methoxy group, an ethoxy group, or an isopropoxy group; and a $C_{3-8}$ cycloalkyl group. However, a substituent group is not limited to these.

In the present specification, the term of "a solvate" means a solvate formed of a fluoroboron compound of the present invention and a solvent. There is no particular limitation on the type of a solvent constituting a solvate and the molar ratio of a solvent to a compound in a solvate.

Preferable examples of a solvate include a hydrate, an alcoholate (such as methanolate, ethanolate, propanolate, or isopropanolate), an ester-adduct (such as ethyl acetate), an ether-adduct (methyl etherate, ethyl etherate, or tetrahydrofuran), and dimethylformamide-adduct. Also, a pharmacologically allowable solvent is preferable.

In the present specification, the term of "a metal catalyst" means a metal and a metal-containing compound which are effective to accelerate an aminomethylation reaction for an aromatic ring, i.e. a coupling reaction, by using a fluoroboron compound as an aminomethylating agent of the present invention. A metal catalyst is not particularly limited, and anything can be used as long as it can accelerate the aforementioned reaction.

Hereinafter, a fluoroboron compound of the present invention and an aminomethylation reaction for an aromatic ring using the same are further described in detail on the basis of specific aspects. However, the present invention is not limited to these specific aspects described below.

[Production Method of Fluoroboron Compound]

A fluoroboron compound represented by the formula (I) is explained herein.

A fluoroboron compound represented by the formula (I) can be produced by using a method represented by reaction formula I described below. However, a production method of a compound of the present invention is not limited to this method.

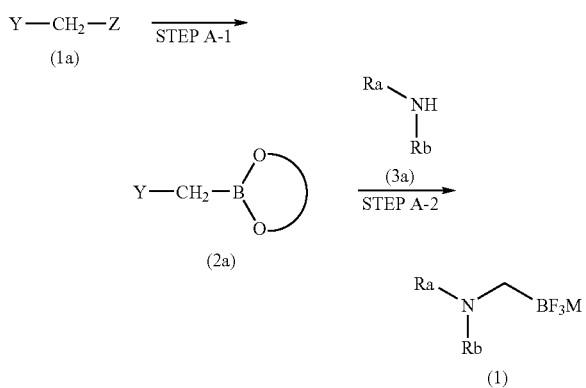

In the formula, Ra, Rb, and M each represents the same as the aforementioned. Y and Z each independently represents a halogen atom.

As a cyclic boronic ester group represented by a formula X, which is a part of the aforementioned formula (2a), cyclic boronic ester groups represented by formulae X-1 to X-6 are exemplified. However, a cyclic boronic ester group represented by a formula X is not limited to these.

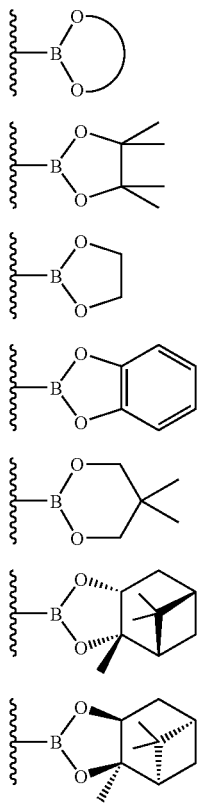

A method of synthesizing a compound represented by the formula (I), which is represented by the aforementioned reaction formula 1, includes 2 steps of the step A-1 and the step A-2 described below.

[Step A-1]

An example of the step A-1 include: reacting an anionized compound, which is produced by the reaction of a compound (1a) and an organic metal reagent selected from n-butyl lithium and so on, and a boronic ester; neutralizing a reaction mixture by adding an acid: and then reacting the reaction mixture with a diol such as pinacol, thereby producing a compound (2a). In the case where the step A-1 is performed, it can be done by referring to the reaction conditions, the post-treatment of the reaction, and the purification method described in Production examples 1 and 2 described below, and it is possible for a person with an ordinary skill in the art to easily decide optimal reaction conditions.

Also, the step A-1 can be performed by adding an organic metal reagent to a mixture including a compound (1a) and a boronic ester, thereby producing an anion from a compound (1a) and reacting an anion with a boronic ester.

The step A-1 can be performed under the stream or the atmosphere of an inert gas such as nitrogen or argon.

As a compound (1a), chloroiodomethane, dibromomethane, and bromoiodemethane can be used, for example. A preferable compound (1a) is chloroiodomethane and dibromomethane.

A solvent used in the step A-1 is not particularly limited as long as it can solve starting materials to an extent and does not inhibit the reaction performed in the step A-1. As a solvent, it is possible to use any solvent selected from the group consisting of an ether-based solvent such as tetrahydrofuran, 1,2-dimethoxyethane, methyl-t-butyl ether, cyclopentyl methyl ether, diethyl ether, diisopropyl ether, dibutyl ether, or dicyclopentyl ether; an aromatic hydrocarbon-based solvent such as benzene or toluene; an aliphatic hydrocarbon-based solvent such as heptane or hexane; and a mixed solvent thereof, for example. A particularly preferable solvent is tetrahydrofuran.

Examples of a boronic ester include trimethyl borate and trilsopropyl borate, but a boronic ester is not limited to these. A particularly preferable boronic ester is triisopropyl borate.

Examples of an organic metal reagent include n-butyl lithium and s-butyl lithium, but the organic metal reagent is not limited to these. A particularly preferable organic metal reagent is n-butyl lithium.

Examples of an acid, which is used to neutralize the reaction mixture, include methanesulfonic acid, p-toluenesulfonic acid, a hydrochloric acid-ethyl acetate solution, and a hydrochloric acid-methanol solution, but an acid is not limited to these. A particularly preferable example is methanesulfonic acid and a hydrochloric acid-ethyl acetate solution.

A reaction time of the step A-1 of the reaction formula I usually varies according to types of used starting materials, a type of a solvent, a type of an organic metal reagent, a type of a used boronic acid, and a reaction temperature, and it is possible for a person with an ordinary skill in the art to easily select a preferable reaction time. For example, a mixture of an anionized compound, which is prepared by using a compound (1a) and an organic metal reagent at −78° C. (an outer temperature of a reaction vessel), and a boronic ester are stirred at a temperature described below for 1 to 3 hours. In addition, the obtained mixture is neutralized at a temperature described below, followed by adding a diol and stirring at a reaction temperature described below for 10 to 60 minutes.

[Reaction Temperature of the Reaction of a Compound, Which is Prepared By Anionizing a Compound (1a), and a Boronic Ester]

A preferable reaction temperature of the reaction of a compound, which is prepared by anionizing a compound (1a), and a boronic ester varies according to types of used starting materials and so on as described above, but this reaction is performed preferably at 0° C. to room temperature (an outer temperature of a reaction vessel), and more preferably at room temperature.

[Reaction Temperature of the Neutralization Reaction and the Reaction With a Diol]

The temperature during neutralizing a mixture obtained by the reaction of a compound, which is prepared by anionizing a compound (1a), and a boronic ester followed by adding a diol thereto is −20° C. to room temperature (an outer temperature of a reaction vessel), and more preferably 0° C. (an outer temperature of a reaction vessel). The temperature after adding a diol to a reaction mixture is 0° C. to room temperature (an outer temperature of a reaction vessel), and more preferably at room temperature.

[Used Amounts of an Organic Metal Reagent and a Boronic Ester]

The aforementioned organic metal reagent is used preferably at 0.8 to 1.2 mol, and more preferably at 0.8 to 1 mol, per 1 mol of a compound (1a).

A boronic ester is used preferably at 0.8 to 1.2 mol, and more preferably at 0.9 to 1 mol, per 1 mol of a compound (1a).

[Step A-2]

The step A-2 include: reacting an anionized compound, which is produced by the reaction of a compound (3a) and a base, and a compound (2a) in a solvent; and then reacting this reaction mixture with a hydrogen fluoride salt selected from potassium hydrogen fluoride and sodium hydrogen fluoride, thereby producing a compound (1). More specifically, this step is performed by referring to the reaction conditions, the post-treatment of the reaction, and the purification method described in Examples A1 to A-6 described below. In addition, it is possible for a person with an ordinary skill in the art to select appropriate reaction conditions and purification method according to types of used starting materials and so on.

The step A-2 can be performed under the stream or the atmosphere of an inert gas such as nitrogen or argon.

As a compound (3a), it is possible to use any compound selected from a commercially available compound and a well-known compound, and compounds produced by using these compounds with a well-known method.

When an anionized compound prepared by the reaction of a compound (3a) and a base is commercially available, this compound can be used for the reaction as it is.

Examples of the base to be reacted with a compound (3a) include sodium hydride, potassium bis(trimethylsilyl)amide, and potassium hydride, and sodium hydride and potassium bis(trimethylsilyl)amide are particularly preferable.

A solvent used in the step A-2 is not particularly limited as long as it can solve used starting materials to an extent and does not inhibit the reaction. As a solvent, it is possible to use any solvent selected from the group consisting of an ether-based solvent such as tetrahydrofuran, 1,2-dimethoxyethane, methyl-t-butyl ether, cyclopentyl methyl ether, diethyl ether, diisopropyl ether, dibutyl ether, or dicyclopentyl ether; an aromatic hydrocarbon-based solvent such as benzene or toluene; an amide-based solvent such as N,N-dimethylformamide or N-methylpyrrolidinone; dimethylsulfoxide; and a mixed solvent thereof, for example. A particularly preferable solvent is tetrahydrofuran and N,N-dimethylformamide.

A reaction time of the step A-2 varies according to types of used starting materials, a type of a used solvent, a type of a reagent, and a reaction temperature, and it is possible for a person with an ordinary skill in the art to appropriately select a preferable reaction time. For example, a compound (3a) is anionized by a base, and then stirred at a reaction temperature described below for 30 to 60 minutes. In addition, a compound (2a) is added to the obtained mixture, followed by stirring at a reaction temperature described below for 1 to 12 hours.

[Reaction Temperature of the Reaction for Anionizing a Compound (3a) With a Base]

A reaction temperature of this reaction usually varies according to types of used starting materials, a type of a used solvent, and a type of a base used in the reaction, and it is possible for a person with an ordinary skill in the art to appropriately select a preferable reaction time. For example, a reaction temperature after adding a base is preferably −78° C. to 70° C. (an outer temperature of a reaction vessel), and more preferably 0° C. to room temperature (an outer temperature of a reaction vessel).

[Reaction Temperature of the Reaction of a Compound, Which is Prepared by Anionizing a Compound (3a), and a Compound (2a)]

A reaction temperature of this reaction usually varies according to types of used starting materials, a type of a used solvent, and a type of a reagent used in the reaction, and it is possible for a person with an ordinary skill in the art to appropriately select a preferable reaction time. For example, a reaction temperature during adding a compound (2a) to the reaction mixture is preferably 0° C. to room temperature (an outer temperature of a reaction vessel), and more preferably 0° C. (an outer temperature of a reaction vessel).

Also, a reaction temperature after adding a compound (2a) is preferably 0° C. to 100° C. (an outer temperature of a reaction vessel), and more preferably 0° C. to 70° C. (an outer temperature of a reaction vessel).

[Reaction Temperature of the Reaction in Which a Hydrogen Fluoride is Added]

As described above, a compound (3a) is anionized with a base, reacted by adding a compound (2a), and then reacted by further adding a hydrogen fluoride salt to the reaction mixture, thereby converting a boronic ester residue to a trifluoroborate.

A reaction temperature of this reaction usually varies according to types of used starting materials, a type of a used solvent, and a type of a reagent used in the reaction, and it is possible for a person with an ordinary skill in the art to appropriately select a preferable reaction time. For example, a reaction temperature during adding a hydrogen fluoride salt to the reaction mixture is 0° C. to room temperature (an outer temperature of a reaction vessel), and more preferably 0° C. (an outer temperature of a reaction vessel).

A reaction temperature after adding a hydrogen fluoride salt is preferably 0° C. to room temperature (an outer temperature of a reaction vessel), and more preferably room temperature (an outer temperature of a reaction vessel).

[Used Amount of a Base]

The aforementioned base, which is used to anionize a compound (3a), is used preferably at 1 to 2 mol-equivalent, and more preferably at 1 to 1.8 mol-equivalent, per 1 mol of a compound (3a).

[Used Amounts of a Compounds (2a) and (3a)]

Also, in this reaction, a compound (3a) is used preferably at 1 to 10 mol-equivalent, and more preferably at 1 to 1.8 mol-equivalent, per 1 mol of a compound (2a).

[Used Amount of a Hydrogen Fluoride]

The aforementioned hydrogen fluoride is used preferably at 2 to 8 mol-equivalent, and more preferably at 2 to 6 mol-equivalent, per 1 mol of a compound (2a).

[Formation of a Dimer]

In the case where Rb in the formula (I) is a hydrogen atom, 2 molecules of a compound represented by the formula (I) are combined into one, thereby forming a dimer represented by a formula (II).

(II)

(In the formula, Ra and M represent the same as the aforementioned)

[Preparation of a Tetraalkylammonium Salt and a Tetraalkylphosphonium Salt]

In the case where M in a compound (I) is an alkali metal ion, this compound (I) can be farther reacted with a reactant selected from a tetraalkylammonium hydroxide, a tetraalkylphosphonium hydroxide, and so on, thereby being converted into a compound (I) in which M represents $[N(R^1)(R^2)(R^3)(R^4)]^+$ or $[P(R^1)(R^2)(R^3)(R^4)]^+$ ($R^1$, $R^2$, $R^3$ and $R^4$ each independently represents a $C_{1-6}$ alkyl group or a $C_{7-15}$ aralkyl group). This step can be performed by referring to the method described in Tetrahedron Letters, Vol. 42, pp. 9099-9103.

Examples of a tetraalkylammonium hydroxide include tetrabutylammonium hydroxide. Also, examples of a tetraalkylphosphonium hydroxide include tetrabutylphosphonium hydroxide.

As a solvent, which is used in the reaction to convert M from an alkali metal ion to a tetraalkylammonium salt or a tetraalkylphosphonium salt, a mixed solvent of dichloromethane or chloroform, and water can be used.

A reaction time of this salt-exchange reaction is usually 1 to 30 min, and preferably 1 to 5 min, at room temperature (an outer temperature of a reaction vessel).

Also a reaction temperature of the salt-exchange reaction is usually 10° C. to 50° C., and preferably room temperature (each is an outer temperature of a reaction vessel).

[(Aminomethylation Reaction Using a Fluoroboron Compound of the Present Invention]

As described above, a compound (I) of the present invention can be used as an aminomethylating agent for an aromatic compound. By using this reaction, an aminomethyl group can be introduced to an aromatic ring in one step. Hereinafter, this reaction is described.

A scheme of an aminomethylation reaction for an aromatic ring, which uses a compound (I) of the present invention as an aminomethylating agent, is represented by the reaction formula 2.

The coupling reaction is performed under the presence of a metal catalyst which is effective as a catalyst for this reaction. Examples of a metal catalyst include a metal such as a palladium metal, a platinum metal, a nickel metal, a rhodium metal, and an iridium metal; and a compound containing a metal selected from these metals. As a metal catalyst, a palladium metal is preferable. Specific examples of a palladium metal include palladium(II) acetate, tris(dibenzylideneacetone)dipalladium (0), palladium carbon, bis(triphenylphosphine)palladium(II) chloride, bis(tri-t-butylphosphine)palladium(0), tetrakis(triphenylphosphine)palladium(0), and 1,1'-bis(diphenylphosphinoferrocene)dichloropalladium(II), while palladium(II) acetate is most preferable.

The aforementioned metal catalyst is used preferably at 0.001 to 5 mol-equivalent, and more preferably at 0.05 to 0.2 mol-equivalent, per 1 mol of an aromatic ring-containing compound (1b).

It is particularly preferable that the coupling reaction be performed under the presence of a base and a phosphine compound together with the aforementioned metal catalyst.

Examples of the base include potassium phosphate tribasic, cesium carbonate, and cesium fluoride. Of these, cesium carbonate and potassium phosphate tribasic are preferable bases.

REACTION FORMULA 2

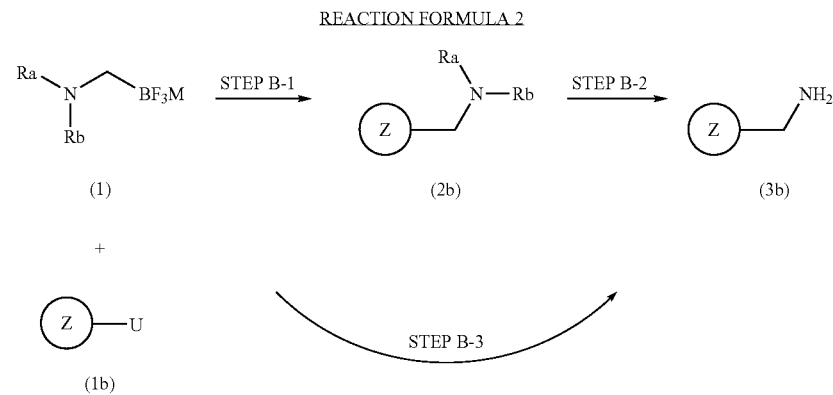

In the reaction formula, Ra, Rb, M, and X represent the same as in a compound represented by the formula (I) as described above. U represents a leaving group such as a halogen group or a trifluoromethanesulfonyloxy group.

A compound (1b) represents an aromatic ring which is capable of cause a coupling reaction with an aminomethylating agent of the present invention. In the present specification, as described above, an aromatic ring includes a hydrocarbon-based aromatic ring such as a benzene ring, a naphthalene ring, or a heteroaryl ring such as pyrrole, pyridine, or quinoline.

[Step B-1]

The step B-1 of the reaction formula 2 is a step of performing the coupling reaction of an aromatic ring-containing compound (1b) and a fluoroboron compound (I) in an appropriate solvent, thereby producing a compound (2b). For convenience of following explanation, only a compound (I) is described in the reaction formula 2. However, instead of a compound (I), a compound (II) or a compound (III) can be used in an aminomethylation reaction for an aromatic ring.

As a compound (1b), it is possible to use any compound selected from a commercially available compound and a well-known compound, and compounds produced by using these compounds with a well-known method.

A base is used preferably at 1 to 4 mol-equivalent, and more preferably at 2 to 3 mol-equivalent, per 1 mol of a fluoroboron compound (I), (II), or (III) of the present invention.

Examples of the phosphine compound include triphenylphosphine, tri-o-tolylphosphine, tri-t-butylphosphine, tricyclohexylphosphine, diphenylphosphinoferrocene, 2-dicyclohexylphosphino-2',6'-dimethoxybiphenyl, 2-dicyclohexylphosphino-2',4',6'-triisopropylbiphenyl, 2-di-t-butylphosphino-2',4',6'-triisopropylbiphenyl, 2-di-t-butylphosphinobiphenyl, 2-dicyclohexylphosphinobiphenyl, 2-dicyclohexylphosphino-2'-(N,N-dimethylamino)biphenyl, 2-di-t-butylphosphino-2'-(N,N-dimethylamino)biphenyl, 2,2-bis(diphenylphosphino)-1,1'-binaphthyl, 1,2-bis(diphenylphosphino)ethane, 1,3-bis(diphenylphosphino)propane, and 1,4-bis(diphenylphosphino)butane, and 2-dicyclohexylphosphino-2',6'-dimethoxybiphenyl is particularly preferable.

A phosphine compound is used preferably at 0.001 to 3 mol-equivalent, and more preferably at 0.05 to 0.8 mol-equivalent, per 1 mol of a fluoroboron compound (I), (II), or (III) of the present invention.

In the step B-1, a compound (I) is used preferably at 1 to 3 mol-equivalent, and more preferably at 1 to 2 mol-equivalent, per 1 mol of a compound (1b). The same applies in the case where a compound (II) or (III) is used instead of a compound (I).

In the case where the step B-1 is performed, a solvent may be used, and there is no particular limitation thereon as long as it can solve starting materials to an extent and does not inhibit the reaction. Examples of a solvent, which can be used in the step B-1, include an ether-based solvent such as tetrahydrofuran, 1,2-dimethoxyethane, methyl-t-butyl ether, cyclopentyl methyl ether, diethyl ether, diisopropyl ether, dibutyl ether, or dicyclopentyl ether; an aromatic hydrocarbon-based solvent such as benzene or toluene; an aliphatic hydrocarbon-based solvent such as heptane or hexane; an amide-based solvent such as N,N-dimethylformamide or N-methylpyrrolidinone; dimethylsulfoxide; and a mixed solvent thereof. A particularly preferable solvent is 1,4-dioxane or toluene.

Regarding details of the step B-1 such as reaction conditions, a post-treatment, or a purification method, it is possible for a person with an ordinary skill in the art to easily decide them by referring to the conditions described in following Examples B1 to B9. Also, in the case where starting materials and an aminomethylating agent other than those described in Examples are used, it is possible for a person with an ordinary skill in the art to easily decide optimal conditions for performing the reaction.

A reaction temperature and a reaction time of the step B-1 varies according to types of used starting materials, a type of a used solvent, and a type of a reagent used in the reaction, and it is possible for a person with an ordinary skill in the art to appropriately decide an optimal reaction temperature and an optimal reaction time. In general, a reaction temperature is preferably 50° C. to 140° C. (an outer temperature of a reaction vessel), and more preferably 95° C. to 105° C. (an outer temperature of a reaction vessel). In general, after mixing all starting materials, it is preferable that the reaction be performed for 1 to 72 hours, and more preferably 4 to 20 hours, under stirring.

This reaction can be performed under the stream or the atmosphere of an inert gas such as nitrogen or argon.

By the reaction of the step B-1, a compound (2b) can be obtained, in which an aminomethyl group is introduced to an aromatic ring of a compound (1b).

[Step B-2]

The step B-2 is the step of deprotecting Ra, or Ra and Rb so as to obtain a compound (3b) containing a primary aminomethyl group in the case where Ra represents a protecting group of an amino group and Rb represents a hydrogen atom, or where Both of Ra and Rb represent a protecting group of an amino group. This step can be performed by an optional choice. Also, in the case where either of Ra or Rb represents a protecting group and the other represents a $C_{1-6}$ alkyl group for example, a compound containing a secondary amino group can be obtained by removing a protecting group in the same way as the step B-2.

The step B-2 can be performed by using a well-known removal method of a protecting group of an amino group. For example, in the case where Ra represents a t-butoxycarbonyl group, a deprotection of an amino group can be performed by using the method described in Synthesis, pp. 66-68, 1999. Also, in the case where Ra represents a formyl group, a deprotection of an amino group can be performed by using the method described in Tetrahedron Letters, Vol. 33, pp. 8125-8126. Also, in the case where Ra and Rb represent a phthalimide group formed by joining a nitrogen atom bonded with Ra and Rb, a deprotection of an amino group can be performed by using the method described in Tetrahedron, Vol. 60, pp. 4773-4780.

[Step B-3]

The step B-3 is a step of reacting an aromatic ring-containing compound (1b) and a fluoroboron compound (I) in a solvent, thereby producing a compound (3b) in one-pot. In the step B-3, the coupling reaction of a compound (1b) and a compound (I) is performed under the same conditions as in the aforementioned step B-1, and then a deprotection of an amine-protecting group is performed in the reaction system without isolating a product, thereby obtaining a compound (3b) directly. Optimal conditions for a deprotection of an amine-protecting group vary according to a type of a protecting group, while a deprotection of an amine group can be performed by referring to the conditions described in the references recited in the aforementioned step B-2. Examples of preferable conditions for a deprotection of an amine group include a method in which a hydrazine compound such as hydrazine hydrate is added to the reaction system after the end of a coupling reaction of compounds (1b) and (I); a method in which basicity in the reaction system is increased; and a method of making the reaction system be acidic.

A deprotection of amine using a hydrazine compound can be performed by referring to the reaction conditions, the post-treatment, and the purification method which are described in Examples B1 to B3 described below. In this case, a deprotection of an amine-protecting group can be performed by adding an alcohol-based solvent such as methanol to the reaction mixture.

A reaction time required for a deprotection of amine by using a hydrazine compound varies according to a type of a protecting group, a type of a used solvent, a type of a hydrazine compound used for a deprotection, and a reaction temperature, and it is possible for a person with an ordinary skill in the art to easily decide an appropriate reaction time. This reaction time is usually 30 minutes to 2 hours at 50° C. to 100° C. (an outer temperature of a reaction vessel) under stirring.

A reaction temperature in the case of a deprotection by using a hydrazine compound usually varies according to starting materials, a solvent, and a reagent used in the reaction, and is selected appropriately but is preferably 50° C. to 100° C. (an outer temperature).

In each of the methods or each of the steps, an aimed compound can be isolated from a reaction mixture by using a conventional method after the end of a reaction.

For example, in the case where whole reaction mixture is liquid after a reaction is finished under the heating condition, the reaction mixture is cooled to room temperature or below at request, and is neutralized by appropriately adding an acid or an base to the reaction mixture at room temperature or under cooling (ice-cooling to −78° C.), and/or an oxidizing agent or a reducing agent is added thereto. Subsequently, solvents such as water and ethyl acetate, which are not mutually blended and do not react with an aimed compound, are further added, and a layer containing an aimed compound is separated. Then, an organic solvent, which does not have compatibility with a layer containing an aimed compound and does not react with an aimed compound, is added thereto, and a layer containing an aimed compound is washed and separated. When this layer is an organic layer, this layer is dried with a drying agent such as an anhydrous magnesium sulfate or anhydrous sodium sulfate, a drying agent is removed therefrom, and then a solvent is evaporated, thereby obtaining an aimed compound. Also, when a layer containing an aimed layer is an aqueous layer, this layer is electrically desalinated, and then freeze-dried, thereby obtaining an aimed compound.

Also, in the case where whole reaction mixture is liquid, an aimed compound may be able to be obtained only by evaporating materials other than an aimed compound (such as an solvent or a reagent) under normal or reduced pressure.

Also, in the case where whole reaction mixture is liquid, an aimed compound can be obtained by purifying a reaction mixture with various chromatography (such as thin layer chromatography or column chromatography).

In the case where only an aimed compound is precipitated as a solid in a reaction mixture during reaction, or where only an aimed compound is precipitated as a solid during a treatment of a reaction mixture, firstly, an aimed compound is filtrated by a filtration method. Then, a filtrated aimed compound is washed with an appropriate organic solvent or inorganic solvent such as water, and dried. Subsequently, at request, mother liquor obtained by a filtration operation is processed in the same way as in the case where whole reaction mixture is liquid so that an aimed compound can further be obtained.

Also, in the case where at least one or both of a reagent and a catalyst other than an aimed compound exist as a solid, or where whole reaction mixture is liquid after the end of a reaction, at least one or both of a reagent and a catalyst are precipitated as a solid during a post-treatment, and an aimed compound is dissolved in a solvent, firstly, a reagent and/or a catalyst are isolated by a filtration method. Then, an isolated reagent or catalyst is washed with an appropriate organic solvent or inorganic solvent. Subsequently, a mixed solution obtained by combining an obtained washed solution and mother liquor is processed in the same way as in the case where whole reaction mixture is liquid so that an aimed compound can be obtained.

When materials other than an aimed compound in a reaction mixture do not inhibit a reaction in the next step, these can be used as they are in the next step without isolating an aimed compound.

In an aimed compound produced in accordance with the aforementioned reaction formula 1 or 2, the purity can be increased by appropriately using a recrystallization method, various chromatography methods, or a distillation method according to need.

In the case where an aimed compound is solid, the purity of an aimed compound is usually improved by using a recrystallization method. As a solvent used for a recrystallization method, a single solvent or a mixture of plural solvents can be used, which does not react with an aimed compound. Specifically, firstly, an aimed compound is dissolved in a solvent which does not react with an aimed compound at room temperature or under heating. An obtained solvent is cooled with ice water or left at room temperature so that an aimed compound can be crystallized from this solution.

In the case where an aimed compound is liquid, the purity of an aimed compound is usually improved by using various chromatography methods. In chromatography, for example, weakly-acidic silica gels such as Silica Gel 60 produced by Merck Ltd. (70-230 mesh or 340-400 mesh) or Silica Gel 60 produced by Kanto Chemical Co., Inc. (0.040-0.050 mm) can be used. In the case where an aimed compound is unstable under the acidic condition, neutral Silica Gel 60N produced by Kanto Chemical Co., Inc. (0.10-0.21 mm) can be used. In the case where an aimed compound has basicity, Propylamine-Coating Silica Gel (NH-silica gel column chromatography) produced by Fuji Silysia Chemical Ltd. (200-350 mesh) can be used. Also, in the case where an aimed compound has a zwitterionic structure, or where elution with a high polar solvent such as methanol is necessary, NAM-200H or NAM-300H produced by NAM Laboratory can be used. By using a chromatography with these silica gels, an aimed compound is eluded with a single solvent or a mixed solvent of plural solvents, and a solvent is evaporated from fractions containing an aimed compound so that an aimed compound whose purity is improved can be obtained.

In the case where an obtained compound is liquid, the purity of an aimed compound can be improved by using a distillation method. In a distillation method, an aimed compound can be distillated and purified by depressurizing an aimed compound at room temperature or under heating.

As described above, a method exemplified in the reaction formula 1 is representative as production methods of compounds (I) and (III) of the present invention. In addition, a dimer can be formed from a compound in which at least one of Ra and Rb of a compound (I) represents a hydrogen atom. A formation example of a dimer is described in following Example A-4.

A raw compound and various reagents, which are used to produce a compound of the present invention, may form a salt, a hydrate, or a solvate, and forms thereof may vary according to starting materials and a used solvent, and are not particularly limited as long as its do not inhibit an aimed reaction.

An appropriate type of a used solvent varies according to types of starting materials and a reagent, but is not particularly limited as long as it does not inhibit an aimed reaction and dissolve starting materials to an extent. It is very easy for a person with an ordinary skill in the art to select an appropriate solvent.

In the case where a compound (I) of the present invention is obtained as a free body, at request, a compound (I) may be converted into a salt thereof or a solvate thereof by using a conventional method.

Also, in the case where a compound (I) is obtained as a solvate, after making free amine once, it can be converted into a salt or a solvate again.

Also, various isomers obtained in a compound (I) of the present invention (such as a geometrical isomer, an optical isomer, a rotational isomer, a stereoisomer, or a tautomer) can be purified and isolated by using a conventional separation method such as recrystallization, a diastereomeric salt formation method, an enzymatic resolution, various chromatography (such as thin layer chromatography, column chromatography, or gas chromatography).

EXAMPLES

Hereinafter, the present invention is described in detail on the basis of Examples, but is not limited thereto.

In following Examples, Production examples 1 and 2 are examples of the step A-1 of the reaction formula 1. Also. Examples A1 to A-6are examples of the step A-2 of the reaction formula 1. In addition, Examples B1 to B9 are examples corresponding to the reaction formula 2.

Also, in the following description, the term of (an outer temperature), which represents a reaction temperature, means an outer temperature of a reaction vessel. Also, the term of (an inner temperature) means an inner temperature of a reaction vessel.

Production Example 1

Synthesis of 2-(chloromethyl)-4,4,5,5-tetramethyl-1,3,2-dioxaborolane

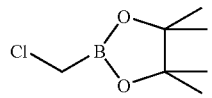

To the mixture of triisopropyl borate (15 ml, 65 mmol), chloroiodomethane (13 g, 72 mmol), and tetrahydrofuran (78 ml), n-butyllithium (a 1.6 M n-hexane solution, 41 ml, 65 mmol) was added dropwise at −78° C. (an outer temperature) for 20 min. and then the obtained mixture was stirred at room temperature for 2.5 hours. The reaction mixture was cooled to 0° C. (an outer temperature), and a 4 N hydrochloric acid-ethyl acetate solution was added dropwise thereto at the same temperature until the reaction mixture became neutral. At the same temperature, pinacol (7.7 g, 65 mmol) was added to the reaction mixture, and then the reaction mixture was stirred at room temperature for 40 min. The solvents were evaporated under reduced pressure, and then the obtained residue was distilled under reduced pressure (63-70° C., 11 mmHg), thereby obtaining the entitled compound (9.2 g, 52 mmol, 81%).

$^1$H-NMR Spectrum (CDCl$_3$) δ(ppm): 1.30(12H, s), 2.97 (2H, s)

Production Example 2

Synthesis of 2-(bromomethyl)-4,4,5,5-tetramethyl-1,3,2-dioxaborolane

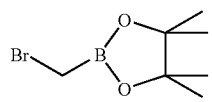

To the mixture of triisopropyl borate (20 g, 110 mmol), dibromomethane (8.6 ml, 120 mmol), and tetrahydrofuran (150 ml), n-butyllithium (a 2.6 M n-hexane solution, 39 ml, 100 mmol) was added dropwise at −78° C. (an outer temperature) for 1.5 hour, and then the reaction mixture was stirred at the same temperature for 1.5 hours. Subsequently, the obtained mixture was stirred at room temperature for 2 hours, and then was cooled to 0° C. (an outer temperature). To the reaction mixture, methanesulfonic acid (6.5 ml, 100 mmol) was added, and then the reaction mixture was stirred at room temperature for 1 hour. The obtained mixture was cooled to 0° C. (an outer temperature), pinacol (12 g, 100 mmol) was added to the reaction mixture, and then the reaction mixture was stirred at room temperature for 1 hour. The solvents were evaporated under reduced pressure from the reaction mixture, and then the obtained residue was distilled under reduced pressure (74-76° C., 8 mmHg), thereby obtaining the entitled compound (16 g, 72 mmol, 68%).

$^1$H-NMR Spectrum (CDCl$_3$) δ(ppm): 1.29(12H, s), 2.59 (2H, s)

Example A1

Synthesis of sodium 1,3-dioxo-1,3-dihydro-isoindole-2-ylmethyl trifluoroborate

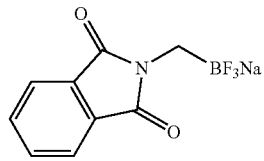

To the mixture of sodium hydride (66%, 84 mg, 2.3 mmol), tetrahydrofuran (2.5 ml), and N,N-dimethylformamide (0.5 ml), the mixture of phthalimide (340 mg, 2.3 mmol), 2-(chloromethyl)-4,4,5,5-tetramethyl-1,3,2-dioxaborolane (410 mg, 2.3 mmol), tetrahydrofuran (2.5 ml), and N,N-dimethylformamide (0.5 ml) was added dropwise at 0° C. (an outer temperature). The obtained mixture was stirred at room temperature overnight. To the reaction mixture, tetrahydrofuran (5 ml) and sodium hydrogen fluoride (720 mg, 12 mmol) were added at 0° C. (an outer temperature), and then water (10 ml) was added dropwise at the same temperature. The reaction mixture was further stirred at room temperature for 1 hour, and then the solvents were evaporated under reduced pressure. To the obtained residue, acetone (100 ml) was added, followed by heating to reflux temperature. The reaction mixture stood to be cooled to about 40° C. (an inner temperature), and then was filtrated. The solvents were evaporated under reduced pressure from the filtrate, and then the residue was washed with the mixed solvent (2:1) of ethyl acetate and tetrahydrofuran, thereby obtaining the entitled compound (240 mmol, 42%).

$^1$H-NMR Spectrum (DMSO-d$_6$) δ(ppm): 2.56(2H, q, J=5.1 Hz), 7.74(4H, s)

Example A2

Synthesis of potassium 1,3-dioxo-1,3-dihydro-isoindole-2-ylmethyl trifluoroborate

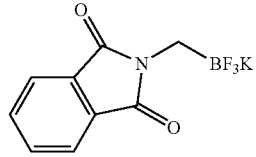

To the mixture of a phthalimide potassium salt (2.8 g, 15 mmol) and dimethylsulfoxide (20 ml), 2-(chloromethyl)-4,4,5,5-tetramethyl-1,3,2-dioxaborolane (55%, 3.3 g, 10 mmol) was added dropwise at room temperature. The obtained mixture was stirred at 70° C. for 1 hour. The reaction mixture was cooled to room temperature, potassium hydrogen fluoride (3.9 g, 51 mmol) was added thereto at the same temperature, and then water (20 ml) was added dropwise at the same temperature. The produced solid was removed by filtration, and the solvents other than dimethylsulfoxide were evaporated under reduced pressure. The obtained residue was washed with the mixed solvent (1:1) of diethyl ether and tetrahydrofuran, and acetone (200 ml) was further added to the residue, followed by heating to reflux temperature. The reaction mixture was filtrated, the solvents were evaporated under reduced pressure from the filtrate, and then the residue was washed with ethyl acetate, thereby obtaining the entitled compound (68 mg, 3%).

$^1$H-NMR Spectrum (DMSO-d$_6$) δ(ppm): 2.51-2.54(2H, m), 7.74(4H, s)

Example A3

Synthesis of sodium (diformylamino)methyl trifluoroborate

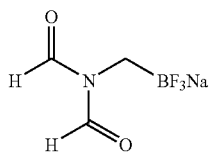

To the mixture of a diformylimide sodium salt (240 mg, 2.5 mmol) and tetrahydrofuran (10 ml), 2-(bromomethyl)-4,4,5,5-tetramethyl-1,3,2-dioxaborolane (92%, 300 mg, 1.3 mmol) was added dropwise at room temperature. The obtained mixture was stirred at 60° C. (an outer temperature) for 20 min. To the reaction mixture, acetonitrile (10 ml) was added at 60° C. (an outer temperature), and it was stirred at the same temperature overnight. Subsequently, the reaction mixture was cooled to 0° C. (an outer temperature), sodium hydrogen fluoride (310 mg, 5.0 mmol) was added thereto at the same temperature, and then water (15 ml) was added dropwise at the same temperature. The solvents were evaporated under reduced pressure from the reaction mixture. To the obtained residue, the mixed solvent (30 ml) of acetone-methanol (20:1) was added and filtrated. The solvents were evaporated under reduced pressure from the filtrate, and then the obtained residue was washed with acetone, thereby obtaining the entitled compound (197 mg) as a crude product. This compound was not purified anymore, and was used as it was for the next reaction.

MS m/e (ESI) 154(M$^-$−Na)

Example A4

Synthesis of disodium 1,4-bis(t-butoxycarbonyl)-2,2,5,5-tetrafluoro-1,4,2,5-diazadiborinane-2,5-diuide

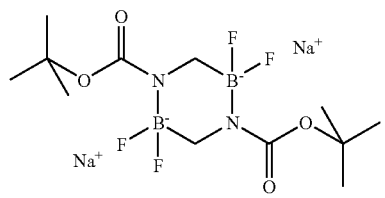

To the mixture of sodium hydride (66%, 91 mg, 2.5 mmol) and tetrahydrofuran (10 ml), di-t-butyl iminodicarboxylate (540 mg, 2.5 mmol) was added dropwise at 0° C. (an outer temperature), followed by stirring at the same temperature for 15 min. To the reaction mixture, 2-(bromomethyl)-4,4,5,5-tetramethyl-1,3,2-dioxaborolane (300 mg, 1.3 mmol) was added, and the obtained mixture was stirred at 60° C. (an outer temperature) overnight. To the reaction mixture, sodium hydrogen fluoride (310 mg, 5 mmol) was added at 0° C. (an outer temperature), and then water (10 ml) was added dropwise at the same temperature. The reaction mixture was stirred at room temperature for 10 min, and then the solvents were evaporated under reduced pressure. To the obtained residue, the mixed solvent (30 ml) of acetone-methanol (20:1) was added, followed by filtration. The solvents were evaporated under reduced pressure from the filtrate, and then the obtained residue was washed with ethyl acetate, thereby obtaining the entitled compound (180 mg, 72%).

$^1$H-NMR Spectrum (DMSO-d$_6$) δ(ppm): 1.42(18H, s), 2.28(4H, t, J=8.1 Hz)

Example A5

Synthesis of potassium morpholine-4-ylmethyl trifluoroborate

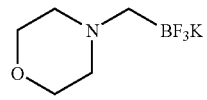

To the mixture of 2-(bromomethyl)-4,4,5,5-tetramethyl-1,3,2-dioxaborolane (1.0 g, 4.5 mmol) and tetrahydrofuran (10 ml), triethylamine (0.70 ml, 5.0 mmol) was added dropwise at 0° C. (an outer temperature), and then morpholine (0.40 ml, 4.5 mmol) was further added dropwise to this reaction mixture. The obtained mixture was stirred at the same temperature for 20 min. Then, a 5 N sodium hydroxide aqueous solution (0.91 ml, 4.5 mmol) was added to the reaction mixture at the same temperature, and the solvents were evaporated under reduced pressure. To the obtained residue, methanol (15 ml) was added, potassium hydrogen fluoride (1.1 g, 14 mmol) was added at room temperature, and then water (1.5 ml) was added dropwise at the same temperature. The reaction mixture was stirred at room temperature for 20 min, and then the solvents were evaporated under reduced pressure. To the obtained residue, acetone (100 ml) and methanol (4 ml) were added, followed by heating to reflux temperature. This mixture stood to be cooled to room temperature, and then was filtrated. The solvents were evaporated under reduced pressure from the filtrate, and then the obtained residue was washed with ethyl acetate, thereby obtaining the entitled compound (144 mg) as a crude product. This compound was not purified anymore, and was used as it was for the next reaction.

Example A6

Synthesis of potassium pyrrolidine-1-ylmethyl trifluoroborate

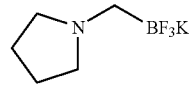

To the mixture of 2-(bromomethyl)-4,4,5,5-tetramethyl-1,3,2-dioxaborolane. (540 mg, 2.3 mmol) and tetrahydrofuran (10 ml), triethylamine (0.63 ml, 4.5 mmol) was added dropwise at 0° C. (an outer temperature), and then pyrrolidine (0.38 ml, 4.5 mmol) was added dropwise to the reaction mixture. The obtained mixture was stirred at room temperature for 2 hours. A 5 N sodium hydroxide aqueous solution (0.45 ml, 2.3 mmol) was added to the reaction mixture at the same temperature, and the solvents were evaporated under reduced pressure. To the obtained residue, methanol (15 ml) was added at 0° C. (an outer temperature), potassium hydrogen fluoride (0.71 g, 9.0 mmol) was added at room temperature, and then water (3 ml) was added dropwise at the same temperature. The reaction mixture was stirred at room temperature for 10 min, and then the solvents were evaporated under reduced pressure. To the obtained residue, acetone (100 ml) and methanol (5 ml) were added, followed by filtration. The solvents were evaporated under reduced pressure from the filtrate, and then the obtained residue was washed with ethyl acetate, thereby obtaining the entitled compound (188 mg) as a crude product.

$^1$H-NMR Spectrum (DMSO-$d_6$) δ(ppm): 1.82-1.95(6H, m), 1.97(2H, q, J=5.0 Hz), 3.09(4H, br s)

Example B1

Synthesis of C-biphenyl-4-yl-methylamine

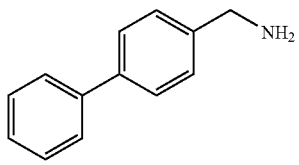

To the mixture of 4-chlorobiphenyl (15 mg, 0.079 mmol) and 1,4-dioxane (1 ml), water (0.1 ml), cesium carbonate (0.16 g, 0.48 mmol), sodium 1,3-dioxo-1,3-dihydro-isoindole-2-ylmethyl trifluoroborate (40 mg, 0.16 mmol), palladium(II) acetate (1.8 mg, 0.0079 mmol), and 2-dicyclohexylphosphino-2',6'-dimethoxybiphenyl (6.5 mg, 0.016 mmol) were added at room temperature, and then the obtained reaction mixture was stirred at 100° C. (an outer temperature) overnight. The reaction mixture was cooled to room temperature, and then hydrazine hydrate (40 mg, 0.79 mmol) and methanol (2 ml) were added thereto, followed by heating to reflux for 30 min. The reaction mixture was cooled to room temperature, and then water and ethyl acetate were added thereto, followed by filtration with celite. The organic layer of the filtrate was separated and washed with saline. The solvents were evaporated under reduced pressure from the organic layer, and then the obtained residue was purified with NH-silica gel column chromatography (ethyl acetate), thereby obtaining the entitled compound (7.7 mg, 53%) as the mixture with 2'-(dicyclohexyl-phosphinoyl)-2,6-dimethoxy-biphenyl (3.8 mg).

$^1$H-NMR Spectrum (DMSO-$d_6$) δ(ppm): 3.76(2H, s), 7.34 (1H, t, J=7.3 Hz), 7.41-7.47(4H, m), 7.59-7.66(4H, m)

Example B2

Synthesis of 2-methoxy-benzylamine

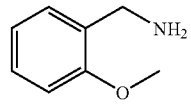

To the mixture of 2-bromoanisole (0.020 ml, 0.16 mmol) and 1,4-dioxane (2 ml), water (0.2 ml), cesium carbonate (0.32 g, 0.97 mmol), sodium 1,3-dioxo-1,3-dihydro-isoindole-2-ylmethyl trifluoroborate (81 mg, 0.32 mmol), palladium(II) acetate (3.6 mg, 0.016 mmol), and 2-dicyclohexylphosphino-2',6'-dimethoxybiphenyl (13 mg, 0.032 mmol) were added, and then the obtained reaction mixture was stirred at 95° C. (an outer temperature) overnight. The reaction mixture was cooled to room temperature, and then hydrazine hydrate (0.039 ml, 0.81 mmol) and methanol (2 ml) were added thereto, followed by heating to reflux for 1 hour. The reaction mixture was cooled to room temperature, and then water and ethyl acetate were added to the reaction mixture, followed by filtration with celite. The organic layer of the filtrate was separated and washed with saline. The solvents were evaporated under reduced pressure from the organic layer, and then the obtained residue was purified with NH-silica gel column chromatography (heptane:ethyl acetate=1:4), thereby obtaining the entitled compound (4.1 mg, 19%) as the mixture with 2'-(dicyclohexyl-phosphinoyl)-2,6-dimethoxy-biphenyl (6.2 mg).

$^1$H-NMR Spectrum (CDCl$_3$) δ(ppm): 3.81(2H, s), 3.85 (3H, s), 6.87(1H, d, J=8.1 Hz), 6.91(1H, dt, J=1.1, 7.3 Hz), 7.20-7.25(2H, m)

Example B3

Synthesis of C-biphenyl-3-yl-methylamine

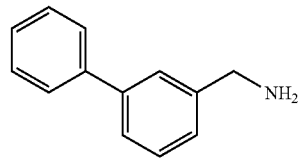

To the mixture of 3-bromobiphenyl (0.020 ml, 0.12 mmol) and 1,4-dioxane (1.5 nil), water (0.15 ml), potassium phosphate tribasic n-hydrate (170 mg, 0.72 mmol), sodium 1,3-dioxo-1,3-dihydro-isoindole-2-ylmethyl trifluoroborate (60 mg, 0.24 mmol), palladium(II) acetate (2.7 mg, 0.012 mmol), and 2-dicyclohexylphosphino-2',6'-dimethoxybiphenyl (9.9 mg, 0.024 mmol) were added, and then the obtained reaction mixture was stirred at 94° C. (an outer temperature) overnight. The reaction mixture was cooled to room temperature, and then hydrazine hydrate (48 mg, 0.96 mmol) and methanol (2 ml) were added thereto, followed by heating to reflux for 40 min. The reaction mixture was cooled to room temperature, and then ethyl acetate and water were added to the reaction mixture, followed by filtration with celite. The organic layer of the filtrate was separated and washed with saline. The solvents were evaporated under reduced pressure from the organic layer, and then the obtained residue was purified with NH-silica gel column chromatography (ethyl acetate), thereby obtaining the entitled compound (11 mg, 51%) as the mixture with 2'-(dicyclohexyl-phosphinoyl)-2,6-dimethoxybiphenyl (6.2 mg).

$^1$H-NMR Spectrum (CDCl$_3$) δ(ppm): 3.95(2H, s), 7.30-7.37(2H, m), 7.40-7.50(4H, m), 7.54-7.55(1H, m), 7.59-7.61 (2H, m)

Example B3

Synthesis of 2-biphenyl-4-ylmethyl-isoindole-1,3-dione

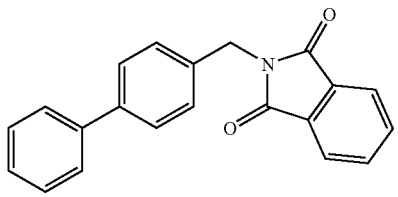

To the mixture of 4-chlorobiphenyl (15 mg, 0.079 mmol) and 1,4-dioxane (1 ml), water (0.1 ml), cesium carbonate (0.16 g, 0.48 mmol), sodium 1,3-dioxo-1,3-dihydro-isoindole-2-ylmethyl trifluoroborate (40 mg, 0.16 mmol), palladium(II) acetate (1.8 mg, 0.0079 mmol), and 2-dicyclohexylphosphino-2',6'-dimethoxybiphenyl (6.5 mg, 0.016 mmol) were added, and then the obtained reaction mixture was stirred at 100° C. (an outer temperature) overnight. The reaction mixture was cooled to room temperature, and then water and ethyl acetate were added to the reaction mixture, followed by filtration with celite. The organic layer of the filtrate was separated and washed with saline. The solvents were evaporated under reduced pressure from the organic layer, and then the obtained residue was purified with silica gel column chromatography (heptane:ethyl acetate=40:1), thereby obtaining the entitled compound (14 mg. 56%).

$^1$H-NMR Spectrum (DMSO-d$_6$) δ(ppm): 4.82(2H, s), 7.33-7.37(1H, m), 7.39-7.47(4H, m), 7.61-7.64(4H, m), 7.86-7.93(4H, m)

Example B5

Synthesis of N-biphenyl-4-ylmethyl-formamide

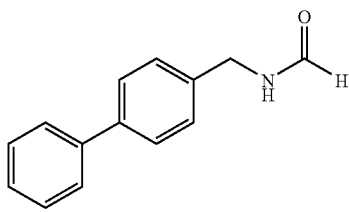

To the mixture of 4-chlorobiphenyl (30 mg, 0.16 mmol) and 1,4-dioxane (1.5 ml), water (0.15 ml), cesium carbonate (0.31 g, 0.95 mmol), sodium (diformylamino)methyl trifluoroborate (a crude compound, 94 mg), palladium(II) acetate (3.6 mg, 0.016 mmol), and 2-dicyclohexylphosphino-2',6'-dimethoxybiphenyl (13 mg, 0.032 mmol) were added at room temperature, and then the obtained reaction mixture was stirred at 100° C. (an outer temperature) overnight. The reaction mixture was cooled to room temperature, and then water and ethyl acetate were added to the reaction mixture, followed by filtration with celite. The organic layer of the filtrate was separated and washed with saline. The solvents were evaporated under reduced pressure from the organic layer, and then the obtained residue was purified with silica gel column chromatography (heptane:ethyl acetate=1:4), thereby obtaining the entitled compound (2.0 mg, 6%).

$^1$H-NMR Spectrum (CDCl$_3$) δ(ppm): 4.55(2H, d, J=5.9 Hz), 7.33-7.39(3H, m), 7.43-7.46(2H, m), 7.57-7.59(4H, m), 8.31(1H, s)

MS m/e (ESI) 234(M$^+$+Na), 266(M$^+$+Na+methanol)

Example B6

Synthesis of biphenyl-4-ylmethyl-carbamic acid t-butyl ester

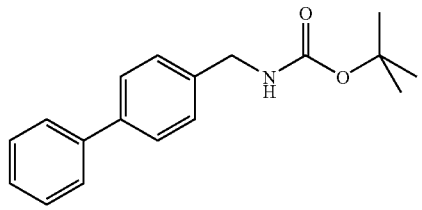

To the mixture of 4-chlorobiphenyl (30 mg, 0.16 mmol) and 1,4-dioxane (1.5 ml), water (0.15 ml), cesium carbonate (0.31 g, 0.95 mmol), disodium 1,4-bis(t-butoxycarbonyl)-2,2,5,5-tetrafluoro-1,4,2,5-diazadiborinane-2,5-diuide (64 mg, 0.16 mmol), palladium(II) acetate (3.6 mg, 0.016 mmol), and 2-dicyclohexylphosphino-2',6'-dimethoxybiphenyl (13 mg, 0.032 mmol) were added at room temperature, and then the obtained reaction mixture was stirred at 100° C. (an outer temperature) overnight. The reaction mixture was cooled to room temperature, and then water and ethyl acetate were added to the reaction mixture, followed by filtration with celite. The organic layer of the filtrate was separated and washed with saline. The solvents were evaporated under reduced pressure from the organic layer, and then the obtained residue was purified with silica gel column chromatography (heptane:ethyl acetate=5:1), thereby obtaining the entitled compound (30 mg, 67%).

$^1$H-NMR Spectrum (CDCl$_3$) δ(ppm): 1.48(9H, s), 4.36 (2H, d, J=5.3 Hz), 4.87(1H, br s), 7.32-7.37(3H, m), 7.42-7.46(2H, m), 7.55-7.59(4H, m)

Example B7

Synthesis of 4-biphenyl-4-ylmethyl-morpholine

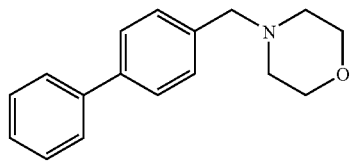

To the mixture of 4-chlorobiphenyl (23 mg, 0.12 mmol) and 1,4-dioxane (2.5 ml), water (0.25 ml), potassium phosphate tribasic n-hydrate (0.28 g, 1.2 mmol), potassium morpholine-4-ylmethyl trifluoroborate (78 mg), palladium(II) acetate (2.7 mg, 0.012 mmol), and 2-dicyclohexylphosphino-2',6'-dimethoxybiphenyl (10 mg, 0.024 mmol) were added at room temperature, and then the obtained reaction mixture was heated to reflux for 10 hours. The reaction mixture was cooled to room temperature, and then water and ethyl acetate were added to the reaction mixture, followed by filtration. The organic layer of the filtrate was separated and washed with saline. The solvents were evaporated under reduced pressure from the organic layer, and then the obtained residue was purified with NH-silica gel column chromatography (heptane:ethyl acetate=5:1), thereby obtaining the entitled compound (20 mg, 64%).

$^1$H-NMR Spectrum (CDCl$_3$) δ(ppm): 2.47-2.49(4H, m), 3.54(2H, s), 3.72-3.74(4H, m), 7.31-7.36(1H, m), 7.39-7.45 (4H, m), 7.54-7.60(4H, m)

Example B8

Synthesis of 4-biphenyl-3-ylmethyl-morpholine

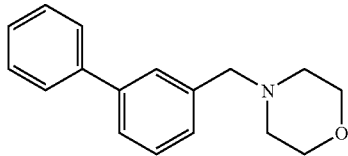

To the mixture of 3-bromobiphenyl (28 mg, 0.12 mmol) and 1,4-dioxane (2.5 ml), water (0.25 ml), potassium phosphate tribasic n-hydrate (0.28 g, 1.2 mmol), potassium morpholine-4-ylmethyl trifluoroborate (78 mg), palladium(II) acetate (2.7 mg, 0.012 mmol), and 2-dicyclohexylphosphino-2',6'-dimethoxybiphenyl (10 mg, 0.024 mmol) were added at room temperature, and then the obtained reaction mixture was heated to reflux for 10 hours. The reaction mixture was cooled to room temperature, and then water and ethyl acetate were added to the reaction mixture, followed by filtration. The organic layer of the filtrate was separated and washed with saline. The solvents were evaporated under reduced pressure from the organic layer, and then the obtained residue was purified with NH-silica gel column chromatography (heptane:ethyl acetate=5:1), thereby obtaining the entitled compound (23 mg, 75%).

$^1$H-NMR Spectrum (CDCl$_3$) δ(ppm): 2.47-2.50(4H, m), 3.57(2H, s), 3.71-3.74(4H, m), 7.31-7.47(5H, m), 7.50(1H, dd, J=0.6, 7.7 Hz), 7.56(1H, s), 7.58-7.62(2H, m)

Example B9

Synthesis of 1-Biphenyl-4-ylmethyl-pyrrolidine

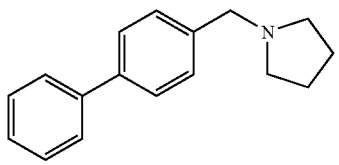

To the mixture of 4-bromobiphenyl (20 mg, 0.086 mmol) and 1,4-dioxane (1.5 ml), water (0.25 ml), potassium phosphate tribasic n-hydrate (0.18 g, 0.73 mmol), potassium pyrrolidine-1-ylmethyl trifluoroborate (40 mg, 0.21 mmol), palladium(II) acetate (3.9 mg, 0.017 mmol), and 2-dicyclohexylphosphino-2',6'-dimethoxybiphenyl (10 mg, 0.034 mmol) were added at room temperature, and then the obtained reaction mixture was stirred at 100° C. for 11 hours. The reaction mixture was cooled to room temperature, and then water and ethyl acetate were added to the reaction mixture, followed by filtration with celite. The organic layer of the filtrate was separated and washed with saline. The solvents were evaporated under reduced pressure from the organic layer, and then the obtained residue was purified with NH-silica gel column chromatography (heptane:ethyl acetate=6:1), thereby obtaining the entitled compound (19 mg, 89%).

$^1$H-NMR Spectrum (CDCl$_3$) δ(ppm): 1.76-1.82(4H, m), 2.52-2.56(4H, m), 3.65(2H, s), 7.31-7.35(1H, m), 7.39-7.45 (4H, m), 7.53-7.60(4H, m)

INDUSTRIAL APPLICABILITY

According to the present invention, a primary, secondary, or tertiary aminomethyl group can be directly introduced to an aromatic ring, and therefore, it is possible to use a substrate which is unstable for a reduction reaction or an aromatic halide such as chlorobenzene which is inexpensive and sold in a market abundantly. Accordingly, the present invention is useful for industrial.

What is claimed is:
1. A compound represented by a formula (III):

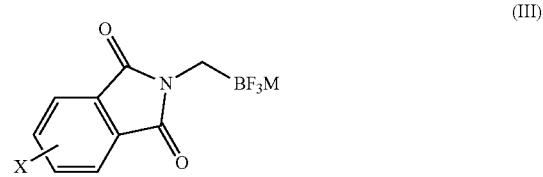

(III)

wherein M represents an alkali metal cation, [N(R$^1$)(R$^2$) (R$^3$)(R$^4$)]$^+$, or [P(R$^1$)(R$^2$) (R$^3$)(R$^4$)]$^+$, R$^1$, R$^2$, R$^3$ and R$^4$ each independently represents a C$_{1-6}$ alkyl group or a C$_{7-15}$ aralkyl group, and X represents a hydrogen atom, a C$_{1-6}$ alkyl group, or a nitro group.

2. A compound according to claim 1, wherein X represents the hydrogen atom.

3. A compound according to claim 1 or 2, wherein M represents the alkali metal cation.

4. A compound according to claim 1 or 2, wherein M represents a potassium ion or a sodium ion.

* * * * *